(12) United States Patent
Ameredes

(10) Patent No.: US 12,133,814 B2
(45) Date of Patent: Nov. 5, 2024

(54) INTRAUTERINE DEVICE REMOVAL SYSTEM PROTECTION APPARATUS

(71) Applicant: Faye Ellen Ameredes, Roseburg, OR (US)

(72) Inventor: Faye Ellen Ameredes, Roseburg, OR (US)

(*) Notice: Subject to any disclaimer, the term of this patent is extended or adjusted under 35 U.S.C. 154(b) by 1160 days.

(21) Appl. No.: 16/554,335

(22) Filed: Aug. 28, 2019

(65) Prior Publication Data

US 2020/0261257 A1    Aug. 20, 2020

Related U.S. Application Data

(60) Provisional application No. 62/806,618, filed on Feb. 15, 2019.

(51) Int. Cl.
*A61F 6/18* (2006.01)

(52) U.S. Cl.
CPC ..................................... *A61F 6/18* (2013.01)

(58) Field of Classification Search
CPC ...... A61F 6/04; A61F 6/065; A61F 2006/042; A61F 6/06; A61F 6/146; A61F 6/14; A61F 5/453; Y10S 128/918; A61H 19/32; A61B 10/0058; A61B 18/149; A61B 18/1487
See application file for complete search history.

(56) References Cited

U.S. PATENT DOCUMENTS 4,815,456 A * 3/1989 Cosentino ................. A61F 6/00
128/206.13
5,723,005 A * 3/1998 Herrick ............... A61F 9/00772
623/4.1

* cited by examiner

*Primary Examiner* — Ophelia A Hawthorne

(57) ABSTRACT

A surgical device for the protection of intrauterine device removal threads during surgical procedures, the device comprising: a shaft having a proximal end and a distal end; and a retriever coupled to the distal end of the shaft and having; a flange projecting therefrom, a proximal aperture, and a distal aperture.

14 Claims, 7 Drawing Sheets

INTRAUTERINE DEVICE REMOVAL SYSTEM PROTECTION APPARATUS

PRIORITY CLAIM

This application claims priority to and/or the benefit of U.S. Provisional Patent Application Ser. No. 62/806,618 filed Feb. 15, 2019. The foregoing application is incorporated by reference in its entirety as if fully set forth herein.

BACKGROUND OF THE INVENTION

This invention relates generally to a medical device, and more specifically, to a device for the protection of intrauterine device ("IUD") removal threads.

BRIEF SUMMARY

This invention relates generally to a medical device, and more specifically, to a device for the protection of intrauterine device removal threads. Specific details of certain embodiments of the invention are set forth in the following description and in the figures to provide a thorough understanding of such embodiments. The present invention may have additional embodiments, may be practiced without one or more of the details described for any particular described embodiment, or may have any detail described for one particular embodiment practiced with any other detail described for another embodiment.

In some embodiments, the invention comprises a shaft and a retriever at the distal end of the shaft with a flange or other means configured to be able to grasp IUD threads. The retriever may be conical in shape, formed by a singular, substantially rectangular piece of a predominantly rigid substance rolled into a cone shape with some space between the overlapping surfaces of the piece. The outer edge of the rolled substance may then be flanged, notched, or otherwise have an excess piece of material protruding off of it. A user or practitioner uses the device by placing the retriever near or inserting the at least the tip of the retriever into the cervix of a patient, and rotating the device so that the flange of the retriever catches the patient's intrauterine device threads and allows them to be pulled into the cone. Inside the cone the threads are protected from damage during surgery.

For example, in a Loop Electrosurgical Excision Procedure ("LEEP"), sometimes referred to as a Large Loop Excision of the Transformation Zone ("LLETZ"), a loop of metal is charged with electricity and used to shave away abnormal tissue from the cervix. During this procedure, the retrieval threads of the IUD can be inadvertently cut, or in certain circumstances cutting the IUD threads may be unavoidable. In those situations, the damaged IUD threads make it difficult for a practitioner to later retrieve or manipulate the IUD and can lead to increased discomfort and cost to a patient. By shielding the IUD removal threads the potential discomfort and cost are prevented. Similarly, in other procedures such as a conization, cold knife conization, or in certain vaginal rejuvenation procedures the devices and tools used can risk damaging the IUD removal threads. The present invention may also be useful in future procedures that take place near or are directed to the cervix.

In some embodiments, the invention is comprised of a material that is not electroconductive in order to prevent any electrical charge from flowing from the loop to the device during a LEEP. In some embodiments the device may be comprised of an electroconductive material for procedures not involving electricity, or where electrical cauterization is not necessary. In some embodiments the device is comprised of one or more materials from the list including, but not limited to, non-conductive metals, plastics, silicone, composites, or glass. In some embodiments, the device is constructed as a single unit, whereas in other embodiments the components of the device may be separate and/or may be comprised of different materials. In some embodiments the device is disposable, while in other embodiments it is meant for repeated use. In some embodiments, specific components of the device, such as the retriever or the shaft are configured to be reused while others may be disposable.

In some embodiments the length of the device and the length of the retriever vary. In some embodiments the device ranges from one inch to eighteen inches long, while the retriever may vary from one-half inch to twelve inches long.

In some embodiments, the retriever is wrapped so that only a small portion of one side overlaps with the other, while in some variations the retriever is a spiral and may wrap around itself numerous times, or only once, depending on the needs of the situation. In some embodiments, the retriever is of a different shape than conical; it may be selected from the list including, but not limited to, cylindrical, frustum, cubic, or pyramidal. The retriever, when unrolled, may take a variety of shapes including, but not limited to, triangle, rectangular, square, circular, a regular or irregular polygon of n sides, or a hybrid or combination thereof.

In some embodiments the shaft is configured to be telescoping or to break on a hinge or other means at specific points in order to reduce or increase its length.

BRIEF DESCRIPTION OF THE DRAWINGS

Embodiments of the present invention are described in detail below with reference to the following drawings.

DETAILED DESCRIPTION

This invention relates generally to a medical device, and more specifically, to a device for the protection of intrauterine device removal threads. Specific details of certain embodiments of the invention are set forth in the following description and in FIGS. 1-7 to provide a thorough understanding of such embodiments. The present invention may have additional embodiments, may be practiced without one or more of the details described for any particular described embodiment, or may have any detail described for one particular embodiment practiced with any other detail described for another embodiment.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

For the purpose of this description, the terms "proximal" and "distal" shall be understood as being in reference to the user of the device. Thus, something described as "proximal" shall be understood to be closer to a user than something that is described as "distal."

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Figure 1:
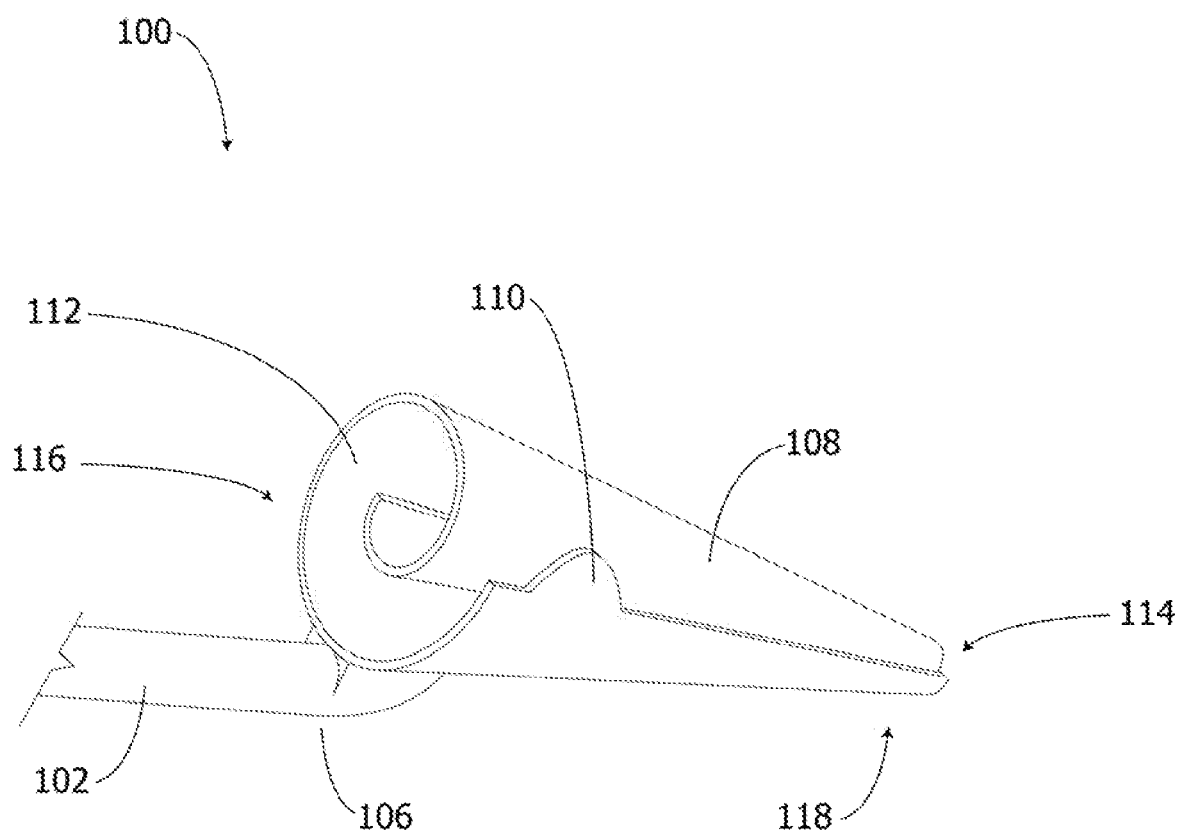
FIG. 1 shows a perspective view of an example of a device for the protection of intrauterine device removal threads.

FIG. 1 shows a perspective view of an example of a device for the protection of intrauterine device removal threads.

In some embodiments, the device for the protection of intrauterine device removal threads 100 comprises a shaft 102 with a proximal end and a distal end 106, and a retriever 108 having a flange 110 projecting therefrom and a proximal aperture 112 and a distal aperture 114, said retriever 108 being coupled to the distal end 106 of the shaft 102. The retriever 108 may be conical in shape, formed by a singular, substantially rectangular piece of a predominantly rigid substance rolled into a cone shape with some space between the overlapping surfaces of the piece. The outer edge of the rolled substance may then be flanged, notched, or otherwise have an excess piece of material protruding off of it as the flange 110. A user or practitioner uses the device 100 by inserting at least the tip of the retriever 108 into and/or near the cervix of a patient and rotating the device so that the flange 110 of the rolled substance catches the patient's intrauterine device ("IUD") threads and allows them to be pulled into the retriever 108. Inside the retriever 108 the threads are protected from damage during surgical procedures.

The flange 110 may project at an angle partially or completely tangential to the edge of the retriever 108, partially or completely perpendicular to the edge of the retriever 108, or at another angle altogether. The flange 110 may be straight; may curve inward following the curve of the retriever 108 or may curve away from the retriever 108; may bend one or more times at an angle along a curved or straight path; or may involve a combination or hybrid thereof. The flange 110 may curve in one or more opposing directions at points along its length; it may have a wave-pattern curve wherein one end is curved different from another, such as in a helix pattern. The flange 110 may have hooks, notches, apertures, or other additional features to facilitate capture of the intrauterine device threads. The aforementioned features may be located anywhere on the flange 110 including, but not limited to, at a proximal or distal end, at any point along an edge, or internal to the flange 110. In some embodiments there may be additional flanges 110 including, but not limited to, two or three additional flanges 110. In some embodiments the flanges 110 may have a smooth edge, or may have a jagged, saw-toothed, or other design of edge. In some embodiments the flange 110 may be a half or quarter circle (or some portion of a circle), square, triangular, or any other polygonal shape.

In some examples the device 100 may be comprised of a material that is not electroconductive in order to prevent any electrical charge from flowing from the loop to the device during a LEEP or other procedure. The device 100 may, in some examples, be comprised of an electroconductive material for procedures not involving electricity, or where electrical cauterization is not necessary. The device 100 may be comprised of one or more materials from the list including, but not limited to, non-conductive metals, plastics, silicone, composites, or glass. Some examples of the device 100 may be constructed as a single unit, whereas in other examples the components of the device may be separate and/or may be comprised of different materials. In some embodiments the device 100 is disposable, while in other embodiments it is meant for repeated use. For some examples, the specific components of the device 100, such as the retriever 108 or the shaft 102 are configured to be reused while others may be disposable.

In some embodiments the length of the device 100 and the length of the retriever 108 vary. In some embodiments the device 100 ranges from one inch to eighteen inches long, while the retriever 108 may vary from one-half inch to twelve inches long. In some embodiments the retriever 108 may be trumpeted in shape, having an uneven profile. In some embodiments the retriever 108 is curved convexly towards its inner axis or concavely away from it; this curve may be even along its length or different shapes. In some embodiments the retriever 108 may be irregularly shaped or otherwise non-symmetrical around an inner axis. In some embodiments the retriever 108 may be curved away from its inner axis at its proximal 116 or distal ends 118.

In some embodiments, the retriever 108 is wrapped so that only a small portion of one side overlaps with the other, while in some variations the retriever 108 is a spiral and may wrap around itself numerous times, or only once, depending on the needs of the situation. In some embodiments, the retriever 108 is of a different shape than conical; it may be selected from the list including, but not limited to, cylindrical, frustum, cubic, or pyramidal. The retriever 108, when unrolled, may take a variety of shapes including, but not limited to, triangle, rectangular, square, circular, a regular or irregular polygon of n sides, or a hybrid or combination thereof. In some embodiments the retriever 108 overlaps itself with a gap of 100 micrometers to 2 centimeters at times it overlaps, though in some embodiments the overlap may vary around the retriever 108 of the device.

In some embodiments the shaft 102 is configured to be telescoping or break on a hinge or other means at specific points in order to reduce or increase its length. In some embodiments the shaft 102 is connected to a handle portion, said handle may be utilized to allow a user to adjust the retriever 108, such as causing it to tighten or close upon a certain activation parameter.

In some examples the device 100 may comprise a substantially cylindrical shaft 102 having a proximal end and a distal end 106; and a retriever 108 comprising a substantially square, flat surface with an outer edge, an inner edge, a top edge, and a bottom edge, rolled into a spiral shape coupled to the distal end 106 of the shaft and having: a semi-circular flange 110 projecting from a proximal point on the outer edge, a proximal aperture 112 formed by the bottom edge, and a distal aperture 114 configured to be smaller than the proximal aperture 112 and formed by the top edge.

Figure 2:
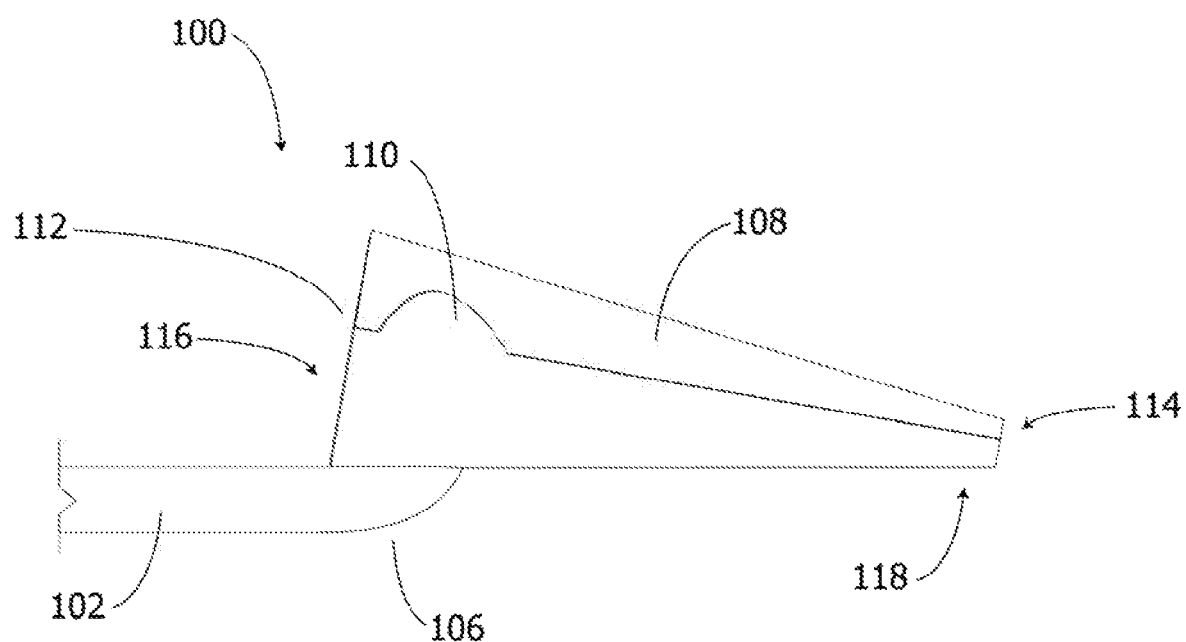
FIG. 2 shows a side view of an example of a device for the protection of intrauterine device removal threads.

FIG. 2 shows a side view of an example of a device for the protection of intrauterine device removal threads.

In some embodiments, the device for the protection of intrauterine device removal threads 100 comprises a shaft 102 with a proximal end and a distal end 106, and a retriever 108 having a flange 110 projecting therefrom and a proximal aperture 112 and a distal aperture 114, said retriever 108 being coupled to the distal end 106 of the shaft 102. The retriever 108 may be conical in shape, formed by a singular, substantially rectangular piece of a predominantly rigid substance rolled into a cone shape with some space between the overlapping surfaces of the piece. The outer edge of the rolled substance may then be flanged, notched, or otherwise have an excess piece of material protruding off of it as the flange 110. A user or practitioner uses the device 100 by inserting at least the tip of the retriever 108 into and/or near the cervix of a patient and rotating the device so that the flange 110 of the rolled substance catches the patient's intrauterine device ("IUD") threads and allows them to be pulled into the retriever 108. Inside the retriever 108 the threads are protected from damage during surgical procedures.

The flange 110 may project at an angle partially or completely tangential to the edge of the retriever 108, partially or completely perpendicular to the edge of the retriever 108, or at another angle altogether. The flange 110 may be straight; may curve inward following the curve of the retriever 108 or may curve away from the retriever 108; may bend one or more times at an angle along a curved or straight path; or may involve a combination or hybrid thereof. The flange 110 may curve in one or more opposing directions at points along its length; it may have a wave-pattern curve wherein one end is curved different from another, such as in a helix pattern. The flange 110 may have hooks, notches, apertures, or other additional features to facilitate capture of the intrauterine device threads. The aforementioned features may be located anywhere on the flange 110 including, but not limited to, at a proximal or distal end, at any point along an edge, or internal to the flange 110. In some embodiments there may be additional flanges 110 including, but not limited to, two or three additional flanges 110. In some embodiments the flanges 110 may have a smooth edge, or may have a jagged, saw-toothed, or other design of edge. In some embodiments the flange 110 may be a half or quarter circle (or some portion of a circle), square, triangular, or any other polygonal shape.

In some examples the device 100 may be comprised of a material that is not electroconductive in order to prevent any electrical charge from flowing from the loop to the device during a LEEP or other procedure. The device 100 may, in some examples, be comprised of an electroconductive material for procedures not involving electricity, or where electrical cauterization is not necessary. The device 100 may be comprised of one or more materials from the list including, but not limited to, non-conductive metals, plastics, silicone, composites, or glass. Some examples of the device 100 may be constructed as a single unit, whereas in other examples the components of the device may be separate and/or may be comprised of different materials. In some embodiments the device 100 is disposable, while in other embodiments it is meant for repeated use. For some examples, the specific components of the device 100, such as the retriever 108 or the shaft 102 are configured to be reused while others may be disposable.

In some embodiments the length of the device 100 and the length of the retriever 108 vary. In some embodiments the device 100 ranges from one inch to eighteen inches long, while the retriever 108 may vary from one-half inch to twelve inches long. In some embodiments the retriever 108 may be trumpeted in shape, having an uneven profile. In some embodiments the retriever 108 is curved convexly towards its inner axis or concavely away from it; this curve may be even along its length or different shapes. In some embodiments the retriever 108 may be irregularly shaped or otherwise non-symmetrical around an inner axis. In some embodiments the retriever 108 may be curved away from its inner axis at its proximal 116 or distal ends 118.

In some embodiments, the retriever 108 is wrapped so that only a small portion of one side overlaps with the other, while in some variations the retriever 108 is a spiral and may wrap around itself numerous times, or only once, depending on the needs of the situation. In some embodiments, the retriever 108 is of a different shape than conical; it may be selected from the list including, but not limited to, cylindrical, frustum, cubic, or pyramidal. The retriever 108, when unrolled, may take a variety of shapes including, but not limited to, triangle, rectangular, square, circular, a regular or irregular polygon of n sides, or a hybrid or combination thereof. In some embodiments the retriever 108 overlaps itself with a gap of 100 micrometers to 2 centimeters at times it overlaps, though in some embodiments the overlap may vary around the retriever 108 of the device.

In some embodiments the shaft 102 is configured to be telescoping or break on a hinge or other means at specific points in order to reduce or increase its length. In some embodiments the shaft 102 is connected to a handle portion, said handle may be utilized to allow a user to adjust the retriever 108, such as causing it to tighten or close upon a certain activation parameter.

Figure 3:
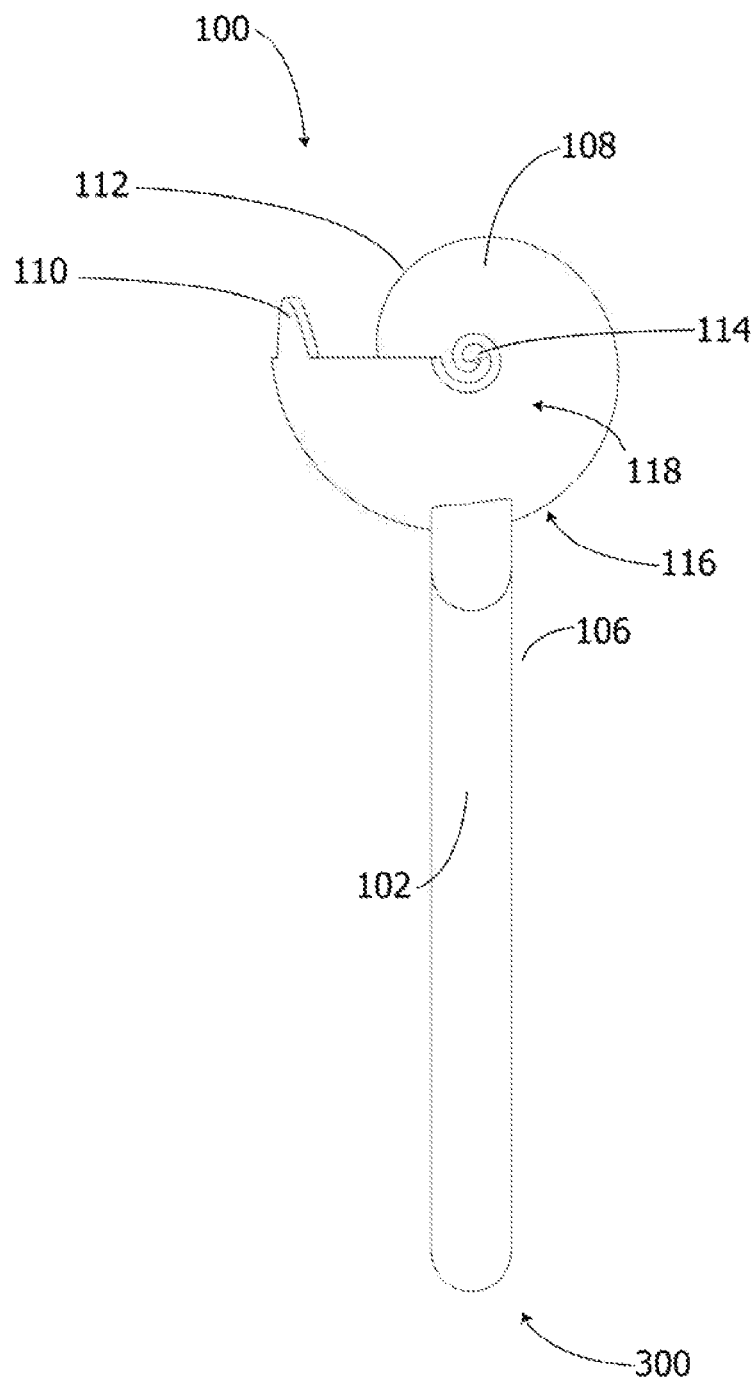
FIG. 3 shows a front view of an example of a device for the protection of intrauterine device removal threads.

FIG. 3 shows a front view of an example of a device for the protection of intrauterine device removal threads.

In some embodiments, the device for the protection of intrauterine device removal threads 100 comprises a shaft 102 with a proximal end 300 and a distal end 106, and a retriever 108 having a flange 110 projecting therefrom and a proximal aperture 112 and a distal aperture 114, said retriever 108 being coupled to the distal end 106 of the shaft 102. The retriever 108 may be conical in shape, formed by a singular, substantially rectangular piece of a predominantly rigid substance rolled into a cone shape with some space between the overlapping surfaces of the piece. The outer edge of the rolled substance may then be flanged, notched, or otherwise have an excess piece of material protruding off of it as the flange 110. A user or practitioner uses the device 100 by inserting at least the tip of the retriever 108 into and/or near the cervix of a patient and rotating the device so that the flange 110 of the rolled substance catches the patient's intrauterine device ("IUD") threads and allows them to be pulled into the retriever 108. Inside the retriever 108 the threads are protected from damage during surgical procedures.

The flange 110 may project at an angle partially or completely tangential to the edge of the retriever 108, partially or completely perpendicular to the edge of the retriever 108, or at another angle altogether. The flange 110 may be straight; may curve inward following the curve of the retriever 108 or may curve away from the retriever 108; may bend one or more times at an angle along a curved or straight path; or may involve a combination or hybrid thereof. The flange 110 may curve in one or more opposing directions at points along its length; it may have a wave-pattern curve wherein one end is curved different from another, such as in a helix pattern. The flange 110 may have hooks, notches, apertures, or other additional features to facilitate capture of the intrauterine device threads. The aforementioned features may be located anywhere on the flange 110 including, but not limited to, at a proximal or distal end, at any point along an edge, or internal to the flange 110. In some embodiments there may be additional flanges 110 including, but not limited to, two or three additional flanges 110. In some embodiments the flanges 110 may have a smooth edge, or may have a jagged, saw-toothed, or other design of edge. In some embodiments the flange 110 may be a half or quarter circle (or some portion of a circle), square, triangular, or any other polygonal shape.

In some examples the device 100 may be comprised of a material that is not electroconductive in order to prevent any electrical charge from flowing from the loop to the device during a LEEP or other procedure. The device 100 may, in some examples, be comprised of an electroconductive material for procedures not involving electricity, or where electrical cauterization is not necessary. The device 100 may be comprised of one or more materials from the list including, but not limited to, non-conductive metals, plastics, silicone, composites, or glass. Some examples of the device 100 may be constructed as a single unit, whereas in other examples the components of the device may be separate and/or may be comprised of different materials. In some embodiments the device 100 is disposable, while in other embodiments it is meant for repeated use. For some examples, the specific components of the device 100, such as the retriever 108 or the shaft 102 are configured to be reused while others may be disposable.

In some embodiments the length of the device 100 and the length of the retriever 108 vary. In some embodiments the device 100 ranges from one inch to eighteen inches long, while the retriever 108 may vary from one-half inch to twelve inches long. In some embodiments the retriever 108 may be trumpeted in shape, having an uneven profile. In some embodiments the retriever 108 is curved convexly towards its inner axis or concavely away from it; this curve may be even along its length or different shapes. In some embodiments the retriever 108 may be irregularly shaped or otherwise non-symmetrical around an inner axis. In some embodiments the retriever 108 may be curved away from its inner axis at its proximal 116 or distal ends 118.

In some embodiments, the retriever 108 is wrapped so that only a small portion of one side overlaps with the other, while in some variations the retriever 108 is a spiral and may wrap around itself numerous times, or only once, depending on the needs of the situation. In some embodiments, the retriever 108 is of a different shape than conical; it may be selected from the list including, but not limited to, cylindrical, frustum, cubic, or pyramidal. The retriever 108, when unrolled, may take a variety of shapes including, but not limited to, triangle, rectangular, square, circular, a regular or irregular polygon of n sides, or a hybrid or combination thereof. In some embodiments the retriever 108 overlaps itself with a gap of 100 micrometers to 2 centimeters at times it overlaps, though in some embodiments the overlap may vary around the retriever 108 of the device.

In some embodiments the shaft 102 is configured to be telescoping or break on a hinge or other means at specific points in order to reduce or increase its length. In some embodiments the shaft 102 is connected to a handle portion, said handle may be utilized to allow a user to adjust the retriever 108, such as causing it to tighten or close upon a certain activation parameter.

Figure 4A:
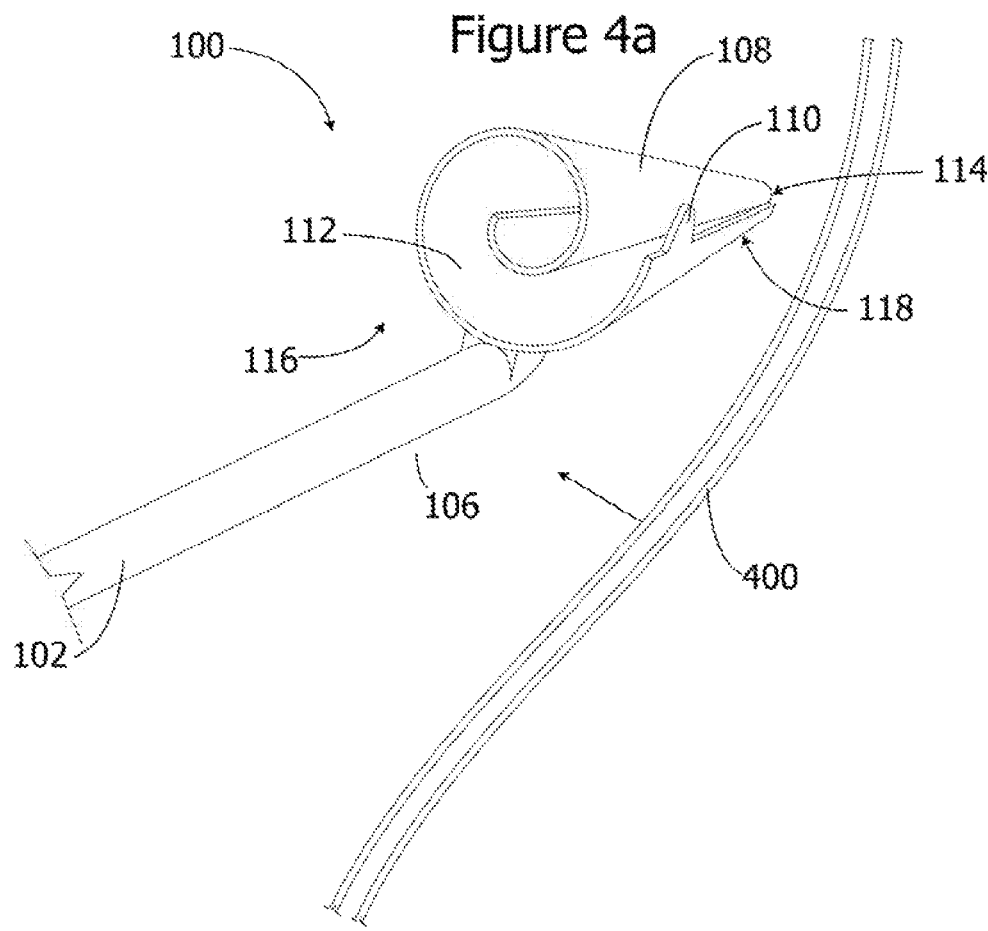
FIG. 4A shows a step in a method of using a device for the protection of intrauterine device removal threads.
Figure 4B:
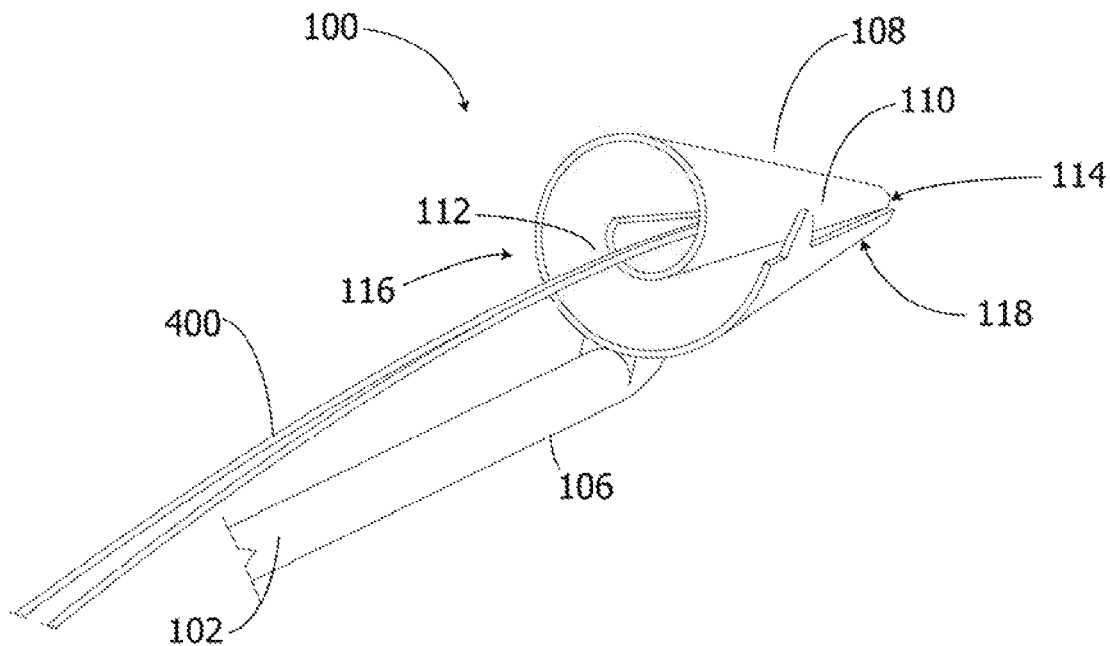
FIG. 4B shows a step in a method of using a device for the protection of intrauterine device removal threads.

FIGS. 4A and 4B show a method of using a device for the protection of intrauterine device removal threads.

In some embodiments, the device for the protection of intrauterine device removal threads 100 comprises a shaft with a proximal end 300 and a distal end 106, and a retriever 108 having a flange 110 projecting therefrom and a proximal aperture 112 and a distal aperture 114, said retriever 108 being coupled to the distal end 106 of the shaft. The retriever 108 may be conical in shape, formed by a singular, substantially rectangular piece of a predominantly rigid substance rolled into a cone shape with some space between the overlapping surfaces of the piece. The outer edge of the rolled substance may then be flanged, notched, or otherwise have an excess piece of material protruding off of it as the flange 110. A user or practitioner uses the device 100 by inserting at least the tip of the retriever 108 into and/or near the cervix of a patient and rotating the device so that the flange 110 of the rolled substance catches the patient's intrauterine device ("IUD") threads and allows them to be pulled into the retriever 108. Inside the retriever 108 the threads are protected from damage during surgical procedures.

The flange 110 may project at an angle partially or completely tangential to the edge of the retriever 108, partially or completely perpendicular to the edge of the retriever 108, or at another angle altogether. The flange 110 may be straight; may curve inward following the curve of the retriever 108 or may curve away from the retriever 108; may bend one or more times at an angle along a curved or straight path; or may involve a combination or hybrid thereof. The flange 110 may curve in one or more opposing directions at points along its length; it may have a wave-pattern curve wherein one end is curved different from another, such as in a helix pattern. The flange 110 may have hooks, notches, apertures, or other additional features to facilitate capture of the intrauterine device threads. The aforementioned features may be located anywhere on the flange 110 including, but not limited to, at a proximal or distal end, at any point along an edge, or internal to the flange 110. In some embodiments there may be additional flanges 110 including, but not limited to, two or three additional flanges 110. In some embodiments the flanges 110 may have a smooth edge, or may have a jagged, saw-toothed, or other design of edge. In some embodiments the flange 110 may be a half or quarter circle (or some portion of a circle), square, triangular, or any other polygonal shape.

In some examples the device 100 may be comprised of a material that is not electroconductive in order to prevent any electrical charge from flowing from the loop to the device during a LEEP or other procedure. The device 100 may, in some examples, be comprised of an electroconductive material for procedures not involving electricity, or where electrical cauterization is not necessary. The device 100 may be comprised of one or more materials from the list including, but not limited to, non-conductive metals, plastics, silicone, composites, or glass. Some examples of the device 100 may be constructed as a single unit, whereas in other examples the components of the device may be separate and/or may be comprised of different materials. In some embodiments the device 100 is disposable, while in other embodiments it is meant for repeated use. For some examples, the specific components of the device 100, such as the retriever 108 or the shaft are configured to be reused while others may be disposable.

In some embodiments the length of the device 100 and the length of the retriever 108 vary. In some embodiments the device 100 ranges from one inch to eighteen inches long, while the retriever 108 may vary from one-half inch to twelve inches long. In some embodiments the retriever 108 may be trumpeted in shape, having an uneven profile. In some embodiments the retriever 108 is curved convexly towards its inner axis or concavely away from it; this curve may be even along its length or different shapes. In some embodiments the retriever 108 may be irregularly shaped or otherwise non-symmetrical around an inner axis. In some embodiments the retriever 108 may be curved away from its inner axis at its proximal 116 or distal ends 118.

In some embodiments, the retriever 108 is wrapped so that only a small portion of one side overlaps with the other, while in some variations the retriever 108 is a spiral and may wrap around itself numerous times, or only once, depending on the needs of the situation. In some embodiments, the retriever 108 is of a different shape than conical; it may be selected from the list including, but not limited to, cylindrical, frustum, cubic, or pyramidal. The retriever 108, when unrolled, may take a variety of shapes including, but not limited to, triangle, rectangular, square, circular, a regular or irregular polygon of n sides, or a hybrid or combination thereof. In some embodiments the retriever 108 overlaps itself with a gap of 100 micrometers to 2 centimeters at times it overlaps, though in some embodiments the overlap may vary around the retriever 108 of the device.

In some embodiments the shaft is configured to be telescoping or break on a hinge or other means at specific points in order to reduce or increase its length. In some embodiments the shaft is connected to a handle portion, said handle may be utilized to allow a user to adjust the retriever 108, such as causing it to tighten or close upon a certain activation parameter.

Figure 5:
FIG. 5 shows a side view of a device for the protection of intrauterine device removal threads.

FIG. 5 shows a side view of a device for the protection of intrauterine device removal threads.

In some embodiments, the device for the protection of intrauterine device removal threads 100 comprises a shaft with a proximal end 300 and a distal end 106, and a retriever 108 having a flange 110 projecting therefrom and a proximal aperture 112 and a distal aperture 114, said retriever 108 being coupled to the distal end 106 of the shaft. The retriever 108 may be conical in shape, formed by a singular, substantially rectangular piece of a predominantly rigid substance rolled into a cone shape with some space between the overlapping surfaces of the piece. The outer edge of the rolled substance may then be flanged, notched, or otherwise have an excess piece of material protruding off of it as the flange 110. A user or practitioner uses the device 100 by inserting at least the tip of the retriever 108 into and/or near the cervix of a patient and rotating the device so that the flange 110 of the rolled substance catches the patient's intrauterine device ("IUD") threads and allows them to be pulled into the retriever 108. Inside the retriever 108 the threads are protected from damage during surgical procedures.

The flange 110 may project at an angle partially or completely tangential to the edge of the retriever 108, partially or completely perpendicular to the edge of the retriever 108, or at another angle altogether. The flange 110 may be straight; may curve inward following the curve of the retriever 108 or may curve away from the retriever 108; may bend one or more times at an angle along a curved or straight path; or may involve a combination or hybrid thereof. The flange 110 may curve in one or more opposing directions at points along its length; it may have a wave-pattern curve wherein one end is curved different from another, such as in a helix pattern. The flange 110 may have hooks, notches, apertures, or other additional features to facilitate capture of the intrauterine device threads. The aforementioned features may be located anywhere on the flange 110 including, but not limited to, at a proximal or distal end, at any point along an edge, or internal to the flange 110. In some embodiments there may be additional flanges 110 including, but not limited to, two or three additional flanges 110. In some embodiments the flanges 110 may have a smooth edge, or may have a jagged, sawtoothed, or other design of edge. In some embodiments the flange 110 may be a half or quarter circle (or some portion of a circle), square, triangular, or any other polygonal shape.

In some examples the device 100 may be comprised of a material that is not electroconductive in order to prevent any electrical charge from flowing from the loop to the device during a LEEP or other procedure. The device 100 may, in some examples, be comprised of an electroconductive material for procedures not involving electricity, or where electrical cauterization is not necessary. The device 100 may be comprised of one or more materials from the list including, but not limited to, non-conductive metals, plastics, silicone, composites, or glass. Some examples of the device 100 may be constructed as a single unit, whereas in other examples the components of the device may be separate and/or may be comprised of different materials. In some embodiments the device 100 is disposable, while in other embodiments it is meant for repeated use. For some examples, the specific components of the device 100, such as the retriever 108 or the shaft are configured to be reused while others may be disposable.

In some embodiments the length of the device 100 and the length of the retriever 108 vary. In some embodiments the device 100 ranges from one inch to eighteen inches long, while the retriever 108 may vary from one-half inch to twelve inches long. In some embodiments the retriever 108 may be trumpeted in shape, having an uneven profile. In some embodiments the retriever 108 is curved convexly towards its inner axis or concavely away from it; this curve may be even along its length or different shapes. In some embodiments the retriever 108 may be irregularly shaped or otherwise non-symmetrical around an inner axis. In some embodiments the retriever 108 may be curved away from its inner axis at its proximal 116 or distal ends 118.

In some embodiments, the retriever 108 is wrapped so that only a small portion of one side overlaps with the other, while in some variations the retriever 108 is a spiral and may wrap around itself numerous times, or only once, depending on the needs of the situation. In some embodiments, the retriever 108 is of a different shape than conical; it may be selected from the list including, but not limited to, cylindrical, frustum, cubic, or pyramidal. The retriever 108, when unrolled, may take a variety of shapes including, but not limited to, triangle, rectangular, square, circular, a regular or irregular polygon of n sides, or a hybrid or combination thereof. In some embodiments the retriever 108 overlaps itself with a gap of 100 micrometers to 2 centimeters at times it overlaps, though in some embodiments the overlap may vary around the retriever 108 of the device.

In some embodiments the shaft is configured to be telescoping or break on a hinge or other means at specific points in order to reduce or increase its length. In some embodiments the shaft is connected to a handle portion, said handle may be utilized to allow a user to adjust the retriever 108, such as causing it to tighten or close upon a certain activation parameter.

Figure 6:
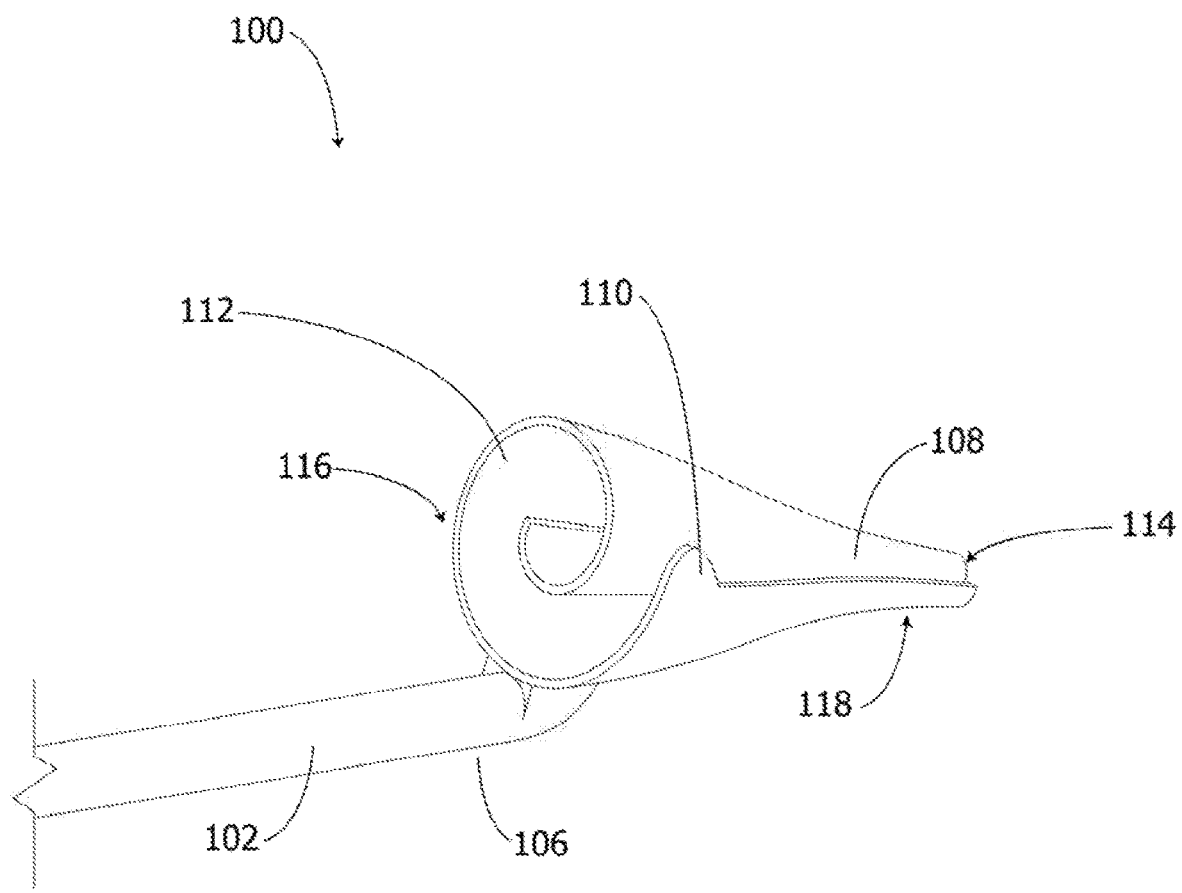
FIG. 6 shows a perspective view of an example of a device for the protection of intrauterine device removal threads.

FIG. 6 shows a perspective view of an example of a device for the protection of intrauterine device removal threads.

In some embodiments, the device for the protection of intrauterine device removal threads 100 comprises a shaft with a proximal end 300 and a distal end 106, and a retriever 108 having a flange 110 projecting therefrom and a proximal aperture 112 and a distal aperture 114, said retriever 108 being coupled to the distal end 106 of the shaft. The retriever 108 may be conical in shape, formed by a singular, substantially rectangular piece of a predominantly rigid substance rolled into a cone shape with some space between the overlapping surfaces of the piece. The outer edge of the rolled substance may then be flanged, notched, or otherwise have an excess piece of material protruding off of it as the flange 110. A user or practitioner uses the device 100 by inserting at least the tip of the retriever 108 into and/or near the cervix of a patient and rotating the device so that the flange 110 of the rolled substance catches the patient's intrauterine device ("IUD") threads and allows them to be pulled into the retriever 108. Inside the retriever 108 the threads are protected from damage during surgical procedures.

The flange 110 may project at an angle partially or completely tangential to the edge of the retriever 108, partially or completely perpendicular to the edge of the retriever 108, or at another angle altogether. The flange 110 may be straight; may curve inward following the curve of the retriever 108 or may curve away from the retriever 108; may bend one or more times at an angle along a curved or straight path; or may involve a combination or hybrid thereof. The flange 110 may curve in one or more opposing directions at points along its length; it may have a wave-pattern curve wherein one end is curved different from another, such as in a helix pattern. The flange 110 may have hooks, notches, apertures, or other additional features to facilitate capture of the intrauterine device threads. The aforementioned features may be located anywhere on the flange 110 including, but not limited to, at a proximal or distal end, at any point along an edge, or internal to the flange 110. In some embodiments there may be additional flanges 110 including, but not limited to, two or three additional flanges 110. In some embodiments the flanges 110 may have a smooth edge, or may have a jagged, saw-toothed, or other design of edge. In some embodiments the flange 110 may be a half or quarter circle (or some portion of a circle), square, triangular, or any other polygonal shape.

In some examples the device 100 may be comprised of a material that is not electroconductive in order to prevent any electrical charge from flowing from the loop to the device during a LEEP or other procedure. The device 100 may, in some examples, be comprised of an electroconductive material for procedures not involving electricity, or where electrical cauterization is not necessary. The device 100 may be comprised of one or more materials from the list including, but not limited to, non-conductive metals, plastics, silicone, composites, or glass. Some examples of the device 100 may be constructed as a single unit, whereas in other examples the components of the device may be separate and/or may be comprised of different materials. In some embodiments the device 100 is disposable, while in other embodiments it is meant for repeated use. For some examples, the specific components of the device 100, such as the retriever 108 or the shaft are configured to be reused while others may be disposable.

In some embodiments the length of the device 100 and the length of the retriever 108 vary. In some embodiments the device 100 ranges from one inch to eighteen inches long, while the retriever 108 may vary from one-half inch to twelve inches long. In some embodiments the retriever 108 may be trumpeted in shape, having an uneven profile. In some embodiments the retriever 108 is curved convexly towards its inner axis or concavely away from it; this curve may be even along its length or different shapes. In some embodiments the retriever 108 may be irregularly shaped or otherwise non-symmetrical around an inner axis. In some embodiments the retriever 108 may be curved away from its inner axis at its proximal 116 or distal ends 118.

In some embodiments, the retriever 108 is wrapped so that only a small portion of one side overlaps with the other, while in some variations the retriever 108 is a spiral and may wrap around itself numerous times, or only once, depending on the needs of the situation. In some embodiments, the retriever 108 is of a different shape than conical; it may be selected from the list including, but not limited to, cylindrical, frustum, cubic, or pyramidal. The retriever 108, when unrolled, may take a variety of shapes including, but not limited to, triangle, rectangular, square, circular, a regular or irregular polygon of n sides, or a hybrid or combination thereof. In some embodiments the retriever 108 overlaps itself with a gap of 100 micrometers to 2 centimeters at times it overlaps, though in some embodiments the overlap may vary around the retriever 108 of the device.

In some embodiments the shaft is configured to be telescoping or break on a hinge or other means at specific points in order to reduce or increase its length. In some embodiments the shaft is connected to a handle portion, said handle may be utilized to allow a user to adjust the retriever 108, such as causing it to tighten or close upon a certain activation parameter.

Figure 7:
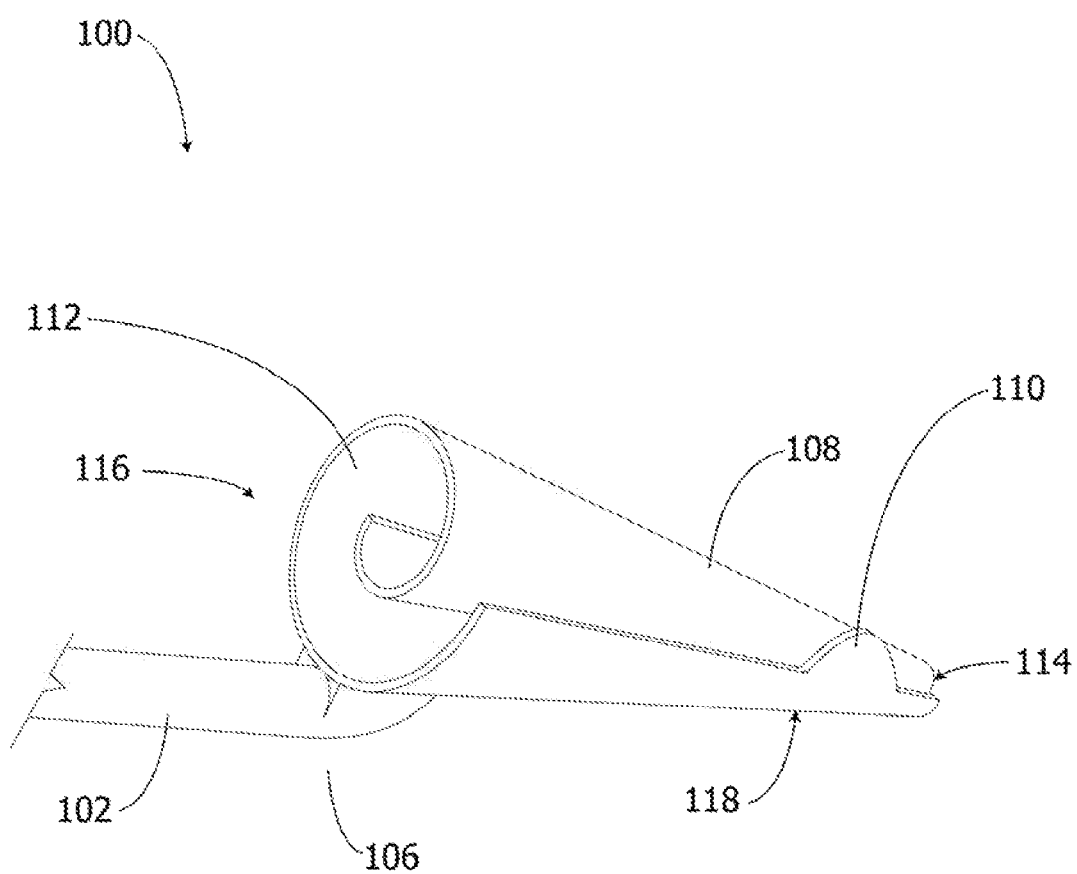
FIG. 7 shows a perspective view of an example of a device for the protection of intrauterine device removal threads.

FIG. 7 shows a perspective view of an example of a device for the protection of intrauterine device removal threads.

In some embodiments, the device for the protection of intrauterine device removal threads 100 comprises a shaft with a proximal end 300 and a distal end 106, and a retriever 108 having a flange 110 projecting therefrom and a proximal aperture 112 and a distal aperture 114, said retriever 108 being coupled to the distal end 106 of the shaft. The retriever 108 may be conical in shape, formed by a singular, substantially rectangular piece of a predominantly rigid substance rolled into a cone shape with some space between the overlapping surfaces of the piece. The outer edge of the rolled substance may then be flanged, notched, or otherwise have an excess piece of material protruding off of it as the flange 110. A user or practitioner uses the device 100 by inserting at least the tip of the retriever 108 into and/or near the cervix of a patient and rotating the device so that the flange 110 of the rolled substance catches the patient's intrauterine device ("IUD") threads and allows them to be pulled into the retriever 108. Inside the retriever 108 the threads are protected from damage during surgical procedures.

The flange 110 may project at an angle partially or completely tangential to the edge of the retriever 108, partially or completely perpendicular to the edge of the retriever 108, or at another angle altogether. The flange 110 may be straight; may curve inward following the curve of the retriever 108 or may curve away from the retriever 108;

may bend one or more times at an angle along a curved or straight path; or may involve a combination or hybrid thereof. The flange 110 may curve in one or more opposing directions at points along its length; it may have a wave-pattern curve wherein one end is curved different from another, such as in a helix pattern. The flange 110 may have hooks, notches, apertures, or other additional features to facilitate capture of the intrauterine device threads. The aforementioned features may be located anywhere on the flange 110 including, but not limited to, at a proximal or distal end, at any point along an edge, or internal to the flange 110. In some embodiments there may be additional flanges 110 including, but not limited to, two or three additional flanges 110. In some embodiments the flanges 110 may have a smooth edge, or may have a jagged, saw-toothed, or other design of edge. In some embodiments the flange 110 may be a half or quarter circle (or some portion of a circle), square, triangular, or any other polygonal shape.

In some examples the device 100 may be comprised of a material that is not electroconductive in order to prevent any electrical charge from flowing from the loop to the device during a LEEP or other procedure. The device 100 may, in some examples, be comprised of an electroconductive material for procedures not involving electricity, or where electrical cauterization is not necessary. The device 100 may be comprised of one or more materials from the list including, but not limited to, non-conductive metals, plastics, silicone, composites, or glass. Some examples of the device 100 may be constructed as a single unit, whereas in other examples the components of the device may be separate and/or may be comprised of different materials. In some embodiments the device 100 is disposable, while in other embodiments it is meant for repeated use. For some examples, the specific components of the device 100, such as the retriever 108 or the shaft are configured to be reused while others may be disposable.

In some embodiments the length of the device 100 and the length of the retriever 108 vary. In some embodiments the device 100 ranges from one inch to eighteen inches long, while the retriever 108 may vary from one-half inch to twelve inches long. In some embodiments the retriever 108 may be trumpeted in shape, having an uneven profile. In some embodiments the retriever 108 is curved convexly towards its inner axis or concavely away from it; this curve may be even along its length or different shapes. In some embodiments the retriever 108 may be irregularly shaped or otherwise non-symmetrical around an inner axis. In some embodiments the retriever 108 may be curved away from its inner axis at its proximal 116 or distal ends 118.

In some embodiments, the retriever 108 is wrapped so that only a small portion of one side overlaps with the other, while in some variations the retriever 108 is a spiral and may wrap around itself numerous times, or only once, depending on the needs of the situation. In some embodiments, the retriever 108 is of a different shape than conical; it may be selected from the list including, but not limited to, cylindrical, frustum, cubic, or pyramidal. The retriever 108, when unrolled, may take a variety of shapes including, but not limited to, triangle, rectangular, square, circular, a regular or irregular polygon of n sides, or a hybrid or combination thereof. In some embodiments the retriever 108 overlaps itself with a gap of 100 micrometers to 2 centimeters at times it overlaps, though in some embodiments the overlap may vary around the retriever 108 of the device.

In some embodiments the shaft is configured to be telescoping or break on a hinge or other means at specific points in order to reduce or increase its length. In some embodiments the shaft is connected to a handle portion, said handle may be utilized to allow a user to adjust the retriever 108, such as causing it to tighten or close upon a certain activation parameter.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects. It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

Accordingly, the scope of the invention is not limited by the disclosure of these preferred and alternate embodiments. Instead, the invention should be determined by reference to the claims that follow.

What is claimed is:

1. A surgical device, the device comprising:
   a shaft having a proximal end and a distal end; and
   a substantially flat retriever that is wrapped around the shaft to form a spiral conical shape without directly contacting the shaft except that an outer face of the retriever is coupled to the distal end of the shaft and having;
      a flange projecting therefrom in a direction perpendicular to the shaft, a proximal aperture comprised of a proximal edge of the retriever, and
      a distal aperture comprised of a distal edge of the retriever where the distal aperture has a radius greater than that of the proximal aperture.

2. The device of claim 1, wherein the shaft is configured to removably couple to the retriever.

3. The device of claim 2, wherein the shaft is removably, frictionally coupled to the retriever.

4. The device of claim 3, wherein the retriever is composed of a disposable material.

5. The device of claim 1, wherein the flange is semicircular in shape.

6. The device of claim 5, wherein the flange follows the contour of the retriever.

7. The device of claim 1, wherein the flange is positioned on an outer edge of the retriever and towards the distal aperture of the retriever.

8. The device of claim 1, wherein the flange is tapered from an inner to an outer edge.

9. The device of claim 1, wherein the retriever is comprised of an at least partially flexible material.

10. The device of claim 1, where the outer surface of the retriever is trumpeted such that there is a sharper curve towards a central point between the proximal aperture and the distal aperture.

11. The device of claim 1, wherein the retriever is composed of a non-conductive material.

12. The device of claim 1, wherein the device is composed of a disposable material.

13. The device of claim 1, wherein the shaft is fixed to the retriever.

14. A surgical device, the device comprising:
   a shaft having a proximal end and a distal end; and
   a substantially flat retriever that is wrapped around the shaft to form a spiral conical
   shape without directly contacting the shaft except that an outer face of the retriever is coupled to the distal end of the shaft and the retriever is further comprised of a first edge opposite a second edge, wherein the second edge has a semi-circular flange extending therefrom wherein the flange is extending perpendicular to the shaft.

* * * * *